US008876528B2

(12) United States Patent
Johnson et al.

(10) Patent No.: US 8,876,528 B2
(45) Date of Patent: Nov. 4, 2014

(54) APPLIANCE FOR DELIVERING LIQUID TO A GAS STREAM FOR CREATING DROPLETS IN A DENTAL CLEANER

(75) Inventors: Ahren Karl Johnson, North Bend, WA (US); Tyler G. Kloster, Snoqualmie, WA (US); Dainia Edwards, Issaquah, WA (US); Wolter F. Benning, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 319 days.

(21) Appl. No.: 13/126,259

(22) PCT Filed: Oct. 30, 2009

(86) PCT No.: PCT/IB2009/054831
§ 371 (c)(1),
(2), (4) Date: Apr. 27, 2011

(87) PCT Pub. No.: WO2010/055435
PCT Pub. Date: May 20, 2010

(65) Prior Publication Data
US 2011/0207078 A1    Aug. 25, 2011

Related U.S. Application Data

(60) Provisional application No. 61/115,190, filed on Nov. 17, 2008.

(51) Int. Cl.
*A61C 17/02* (2006.01)
*A61H 13/00* (2006.01)
*A61C 17/028* (2006.01)

(52) U.S. Cl.
CPC .......... *A61C 17/0217* (2013.01); *A61C 17/028* (2013.01); *A61C 17/0202* (2013.01)
USPC ............................................. 433/88; 601/163

(58) Field of Classification Search
USPC .......... 433/80, 82, 84, 85, 87, 88, 89, 91, 125, 433/215, 216; 239/86, 304, 307, 308, 310, 239/311, 318, 416.4, 416.5, 417.3, 423, 239/424, 424.5; 601/162, 163
See application file for complete search history.

(56) References Cited

U.S. PATENT DOCUMENTS

| 3,137,297 A | | 6/1964 | Maurer et al. | |
| 4,412,402 A | * | 11/1983 | Gallant | ............................ 451/40 |
| 4,771,580 A | * | 9/1988 | Male | .............................. 451/102 |

(Continued)

FOREIGN PATENT DOCUMENTS

| JP | 2007P014730 A | 1/2007 |
| WO | 2005070324 A2 | 8/2005 |

OTHER PUBLICATIONS

Machine translation of JP 2007P014730.*

*Primary Examiner* — Cris L Rodriguez
*Assistant Examiner* — Justin O'Donnell

(57) ABSTRACT

A dental appliance having a passive arrangement for drawing liquid from a reservoir (22, 33, 54) in the appliance by action of a stream of gas, which can be provided by a source of compressed gas (31, 34) or other system. The liquid mixes with the gas, resulting in liquid droplets which are directed through an orifice (18, 42, 68) at the end of a nozzle portion (12, 39, 66) of the appliance.

6 Claims, 2 Drawing Sheets

(56) References Cited

U.S. PATENT DOCUMENTS

| | | |
|---|---|---|
| 4,776,794 A | 10/1988 | Meller |
| 5,820,373 A | 10/1998 | Okano et al. |
| 2003/0027100 A1 | 2/2003 | Grant |
| 2006/0078844 A1 | 4/2006 | Goldman et al. |
| 2007/0095942 A1 | 5/2007 | Ray et al. |
| 2007/0137648 A1 | 6/2007 | Addington et al. |

* cited by examiner

APPLIANCE FOR DELIVERING LIQUID TO A GAS STREAM FOR CREATING DROPLETS IN A DENTAL CLEANER

TECHNICAL FIELD

This invention relates generally to liquid droplet cleaning systems for dental cleaning, and more specifically concerns a system for delivering liquid into a fast-moving gas stream to create the liquid droplets.

BACKGROUND OF THE INVENTION

In general, cleaning of dental (teeth) surfaces with a stream of high-velocity liquid droplets is known. Such systems are particularly useful for cleaning of interproximal spaces. One system for generating the liquid droplets involves merging liquid flowing from a reservoir into a fast-moving gas stream, such as provided by a source of compressed gas. Dental appliances using such systems are activated by a user operating a button or the like, releasing successive bursts of compressed gas, which results in a high velocity gas stream. When this high velocity gas stream comes into contact with a flow of liquid from the reservoir, liquid droplets are produced.

The velocity and size of the droplets can vary, but typically the droplets will have a size in the range of 5-500 microns, and a velocity within a range of 10-200 meters per second. The velocity of the gas stream will also vary; however, a typical range would be 30-600 meters per second. In many cases, liquid is drawn from the liquid reservoir and delivered into the gas stream by a mechanism separate from the flow of gas itself. This results in a higher-cost appliance. It is desirable to have an appliance which produces liquid droplets for cleaning where multiple functions, including the liquid flow and the creation of droplets, can be accomplished by a single, relatively simple system.

SUMMARY OF THE INVENTION

Accordingly the dental cleaning apparatus using liquid droplets, comprises: an appliance body, including a nozzle assembly with a pathway through which a stream of gas is directed and one or more nozzle exit orifices; a source of compressed gas; a reservoir for liquid; and one or more liquid connecting pathways from the liquid reservoir through which liquid in the reservoir can be moved into the stream of gas in the nozzle pathway, wherein the liquid connecting pathways are so configured and have an exit point relative to the stream of gas through the nozzle pathway, that gas moving through the nozzle pathway draws liquid from the liquid reservoir into the stream of gas, resulting in the creation of liquid droplets which then move out through the exit orifice toward the dental regions to be cleaned.

BEST MODE FOR CARRYING OUT THE INVENTION

Figures 1, 2A:
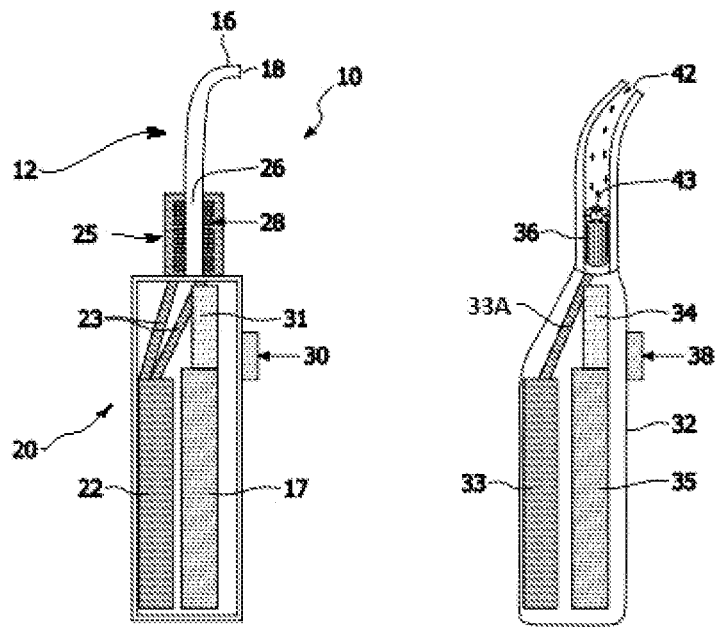
FIG. 1 is a simple schematic view of one embodiment of the present invention.
FIG. 2A is a schematic view of another embodiment of the present invention.

FIG. 1 shows a first embodiment of an interdental cleaner with a passive liquid delivery system. The interdental cleaner, shown generally at 10, includes a nozzle assembly 12 through which fast-moving gas is directed. The appliance includes a power source 17. The gas in the embodiment shown is compressed gas, usually from a cylinder source thereof. Gas volume ranges from 40-650 $mm^3$ at a pressure between 20-900 psi. The nozzle 12 can be shaped at its proximal end portion 16, such as a curve as shown, so as to more conveniently fit into the mouth of a user. The nozzle 12 ends at an exit aperture or apertures 18. Typically, the nozzle opening will be 0.5-2 mm in diameter. Positioned in a base portion 20 of the cleaning appliance assembly is a liquid reservoir member 22, for water or other liquid, including dentifrices. Liquid reservoir 22 is connected by liquid lines 23-23 to a liquid chamber assembly 25 positioned around a lower end portion of nozzle 12. The liquid chamber assembly 25 can have various configurations; for instance, it could be a single member, a plurality of members or can substantially surround the nozzle 12. The length of the liquid reservoir can vary, but typically will be in the range of 2-30 mm.

The liquid chamber assembly includes a plurality of capillary tubes 28, generally positioned horizontally, which connect the liquid chamber assembly 25 to the interior 26 of the nozzle. The capillary tubes 28 will vary in size between 0.25-1 mm in diameter. There could be a single capillary opening or a plurality thereof, all connecting the liquid chamber assembly to the interior 26 of the nozzle. The size of the capillaries must be sufficient to enable liquid to get through during operation of the appliance, but narrow enough to prevent the liquid from leaking out into the nozzle when not in use.

In operation, a single burst of gas will be produced, in response to the operation by the user, of a button 30 or the like, which allows a burst of gas from a source 31 thereof to move into the interior 26 of the nozzle. The movement of gas in the nozzle draws liquid present in the capillaries 28 into the interior 26 of the nozzle.

As the gas moves through the nozzle, past the capillary tube openings, liquid moves into the interior of the nozzle. Typically, approximately 0.02-0.20 ml of liquid will be drawn into interior 26 of the nozzle for a single burst of gas from source 31. Contact between the liquid entering the nozzle from the capillaries with the fast-flowing gas stream will result in the creation of liquid droplets, which move through the forward end of the nozzle and out exit opening 18. Sufficient liquid is drawn from the liquid reservoir with each burst of gas to produce an effective cleansing action on the teeth by the liquid droplets.

The advantage to the arrangement of FIG. 1 is that the delivery of liquid to the gas stream is passive, i.e. there is no separate structure or mechanism for moving liquid from the liquid reservoir into the gas stream other than by the movement of the gas stream itself through the nozzle, with liquid moving into the nozzle by capillary action.

Figure 2B:
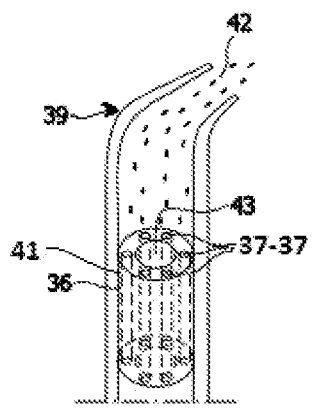
FIG. 2B is a schematic view of a portion of the embodiment of FIG. 2A.

FIGS. 2A and 2B show another passive fluid-delivery interdental system utilizing capillary action. In this arrangement, the appliance includes a base or body portion 32 in which is positioned a liquid reservoir 33. The liquid reservoir in one embodiment is a flexible membrane which allows the reservoir to change volume as liquid is moved from the reservoir into the nozzle portion of the appliance. Also positioned in base portion 32 is a source of compressed gas 34, e.g. a cylinder of $CO_2$ and a power source 35.

Positioned within a mid-portion of the appliance is a hollow sleeve member 36, shown in more detail in FIG. 2B. Sleeve member 36 in the embodiment shown fits in a fluid-tight relationship within the appliance, with a diameter within the range of 1-3 mm and a length of 1-6 mm. The sleeve has a wall portion 41 and a central opening 43 with a wall portion thickness of approximately 0.2-1.2 mm. Positioned lengthwise through the sleeve wall is a series of capillary openings 37-37 which, like the previous embodiment, can be within the range of 0.1-1 mm in diameter. Alternatively, there could be a single capillary, although multiple capillary openings are preferred, spaced evenly around the circumference of the sleeve. The spacing can be varied, however. Extending forward from the mid-portion of the appliance is a nozzle portion 39, typically curved at its proximal region, to readily fit within the mouth. The nozzle terminates in an exit opening 42 having a diameter of 0.5-2 mm.

The user will initiate operation of the appliance by a button switch 38 or the like to actuate bursts of $CO_2$ gas from gas cylinder 34. The resulting gas flow through the open center 43 of sleeve 36 will create a gas flow in nozzle 39, producing a pressure differential within the appliance and pulling liquid from reservoir 33 and liquid line 33A. When the liquid contacts the fast-moving gas, typically moving in the range of 30-60 m/s, liquid droplets are produced, and then accelerated out through exit opening 42 of the nozzle. The droplets, as with the above embodiment, will typically have a size range of 5-500 microns, and a velocity in the range of 10-200 m/s.

Although a compressed $CO_2$ source for the gas stream is shown, it should be understood that other means for producing the gas flow are possible, including a piston/cylinder arrangement or other means, such as a pump to compress air into a valve which is then released, as well as other types of gas, such as nitrogen or air.

The embodiments of both FIGS. 1 and 2 can typically be made from a plastic material such as a polycarbonate, although other materials can be used.

Figure 3:
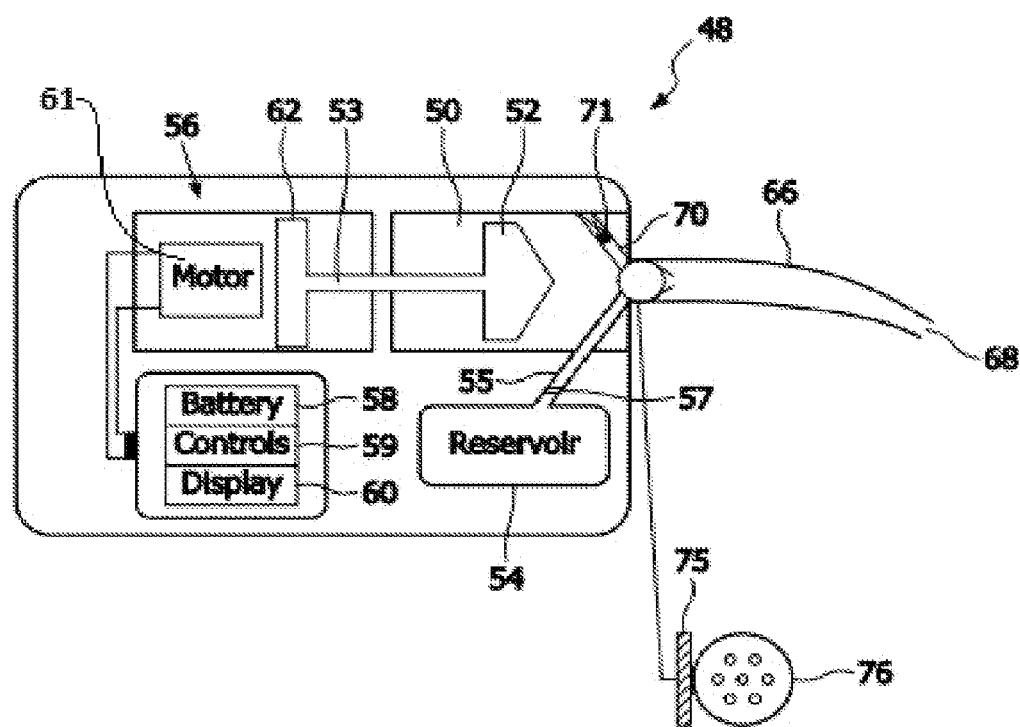
FIG. 3 is a cross-sectional view of still another embodiment of the present invention.

FIG. 3 shows another embodiment of the appliance, referred to generally at 48, which includes an appliance chamber 50. Chamber 50 has a typical diameter of approximately 20 mm, which can be varied, and a length which can vary within the range of 2-25 mm. Positioned within the chamber 50 is a plunger head portion 52 of a plunger assembly, the plunger head portion positioned in a generally fluid-tight arrangement with the internal surface of the chamber 50. A plunger arm 53 extends from a rear end of the plunger head out through a rear opening in chamber 50. The head plunger can move through substantially the length of the chamber. A liquid reservoir 54 is connected by a line 55 to the vicinity of the forward end of chamber 50. A check valve 57 is positioned in the connecting line 55, permitting a flow of liquid in one direction only, i.e. from the reservoir 54 to the chamber 50.

To the rear of chamber 50 in the appliance is a drive assembly 56, which includes a battery 58, as well as control elements 59 and a display 60. Battery 58 powers a motor 61 which drives a drive member 62 which is part of the plunger assembly and is connected to plunger arm 53.

Extending from forward end 62 of chamber 50 is a nozzle 66 which is shaped conveniently to fit within the mouth of a user for dental cleaning. In the embodiment shown, the nozzle is slightly curved. At the distal end of nozzle 66 is an exit opening 68, through which liquid droplets created by action of the gas stream move.

Extending into chamber 50 near the forward end 62 thereof is an air inlet line 70 for entry of atmospheric air. Air inlet line 70 includes a one-way check valve 71, which allows air to proceed only into the chamber. Alternatively, air under some small amount of pressure could be used as well. Positioned at the forward end of chamber 50 at the entrance to the nozzle is a disc member 76 having a number of openings therein. The openings will vary from 0.25-5 mm in diameter. There is also a one-way check valve illustrated generally at 75 between chamber 50 and disc member 76, to prevent air from moving back into the chamber.

In operation, the plunger assembly, including the plunger head, is first withdrawn toward the rear of chamber 50 by action of motor 60, which results in liquid from reservoir 54 being drawn into the chamber and air being drawn into the chamber through inlet 70. Approximately 0.25-2 ml of liquid is drawn from the reservoir upon actuation of the appliance. The plunger is then actuated in the opposing direction to force liquid and air in the chamber through the openings in disc member 76. This action creates droplets at the proximal (base) end of the nozzle 12. The disc 76 can be positioned at the base end of the nozzle or further along the nozzle. The gas pressure created by the action of the plunger also accelerates the droplets once they have been created through the nozzle and out the exit opening 68.

Accordingly, several embodiments of a dental appliance have been disclosed which produce a spray of liquid droplets for use in interdental cleaning, using passive arrangements to draw liquid from a liquid reservoir and to form liquid droplets of desirable size and velocity.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. A dental cleaning apparatus using liquid droplets, comprising:
    an appliance body (20, 32) including a nozzle assembly (12, 39) with an interior pathway (26) through which a stream of gas is directed, and one or more nozzle exit orifices (18, 42);
    a source of compressed gas (31,34);
    a reservoir for liquid (22,33);
    a liquid chamber separate from the nozzle assembly and one or more connecting lines between the reservoir for liquid and the liquid chamber; and
    one or more liquid connecting pathways between the liquid chamber and the nozzle assembly interior pathway or from the liquid chamber into the stream of gas in the nozzle assembly, wherein the one or more liquid connecting pathways are so configured and have an exit point in the nozzle assembly that gas moving through the nozzle assembly interior pathway draws liquid from the liquid reservoir into the liquid chamber and from there into the stream of gas, resulting in the creation of liquid droplets which then move out through the at least one nozzle exit orifice toward the dental regions to be cleaned,
    wherein the appliance body includes a base portion containing the liquid reservoir and the source of compressed gas and wherein the liquid chamber defines a sleeve including a wall portion and a central open portion, the wall portion having a plurality of longitudinal openings therethrough, wherein liquid is drawn from the liquid reservoir into the longitudinal openings by differential pressure created by a flow of gas through the central open portion of the sleeve.

2. The dental cleaning apparatus of claim 1, wherein the one or more liquid connecting pathways include a plurality of capillary tube members extending between the liquid chamber and the nozzle assembly interior pathway.

3. The dental cleaning apparatus of claim 1, wherein a single liquid chamber member substantially surrounds the nozzle assembly.

4. The dental cleaning apparatus of claim 1, wherein the liquid reservoir is collapsible.

5. The dental cleaning apparatus of claim 1, wherein the longitudinal openings are approximately 0.1-1 mm in diameter.

6. The dental cleaning apparatus of claim 1, wherein the sleeve is in the range of 1-6 mm long.

* * * * *